United States Patent [19]

O'Connell et al.

[11] 4,217,780
[45] Aug. 19, 1980

[54] AUTOMATED, SELF-CLEANING FLUID SAMPLING APPARATUS

[75] Inventors: J. Garland O'Connell, Waltham; William C. Reynolds, Dedham, both of Mass.

[73] Assignee: Ortho Diagnostic, Inc., Raritan, N.J.

[21] Appl. No.: 55,877

[22] Filed: Jul. 9, 1979

[51] Int. Cl.² ........................ B01L 3/02; G01N 1/10
[52] U.S. Cl. ................................. 73/421 R; 73/425.6
[58] Field of Search ............... 73/425.6, 423 A, 421 R; 422/63, 64, 100

[56] References Cited

U.S. PATENT DOCUMENTS

| | | | |
|---|---|---|---|
| 3,252,330 | 5/1966 | Kling | 73/423 A |
| 3,552,212 | 1/1971 | Ohlin | 73/423 A |
| 3,604,269 | 9/1971 | Smith | 73/423 A |
| 3,748,911 | 7/1973 | Rousselet | 73/423 A |
| 3,869,068 | 3/1975 | Chen | 422/100 |

*Primary Examiner*—S. Clement Swisher
*Attorney, Agent, or Firm*—Audley A. Ciamporcero, Jr.

[57] ABSTRACT

A fluid sampling nozzle is spatially fixed, and adapted to be supplied by fluid to be sampled. A nearby actuating switch, manipulated by the operator, energizes a sequence of sampling, cleaning, and drying steps. In particular, once fluid is withdrawn, the sample is removed. A waste removal sink pivots to a point beneath the nozzle, and in a series of motions by a probe washer assembly, the nozzle is successively washed, inside and out. The apparatus is then returned to its initial position, ready for successive sampling operations.

5 Claims, 11 Drawing Figures

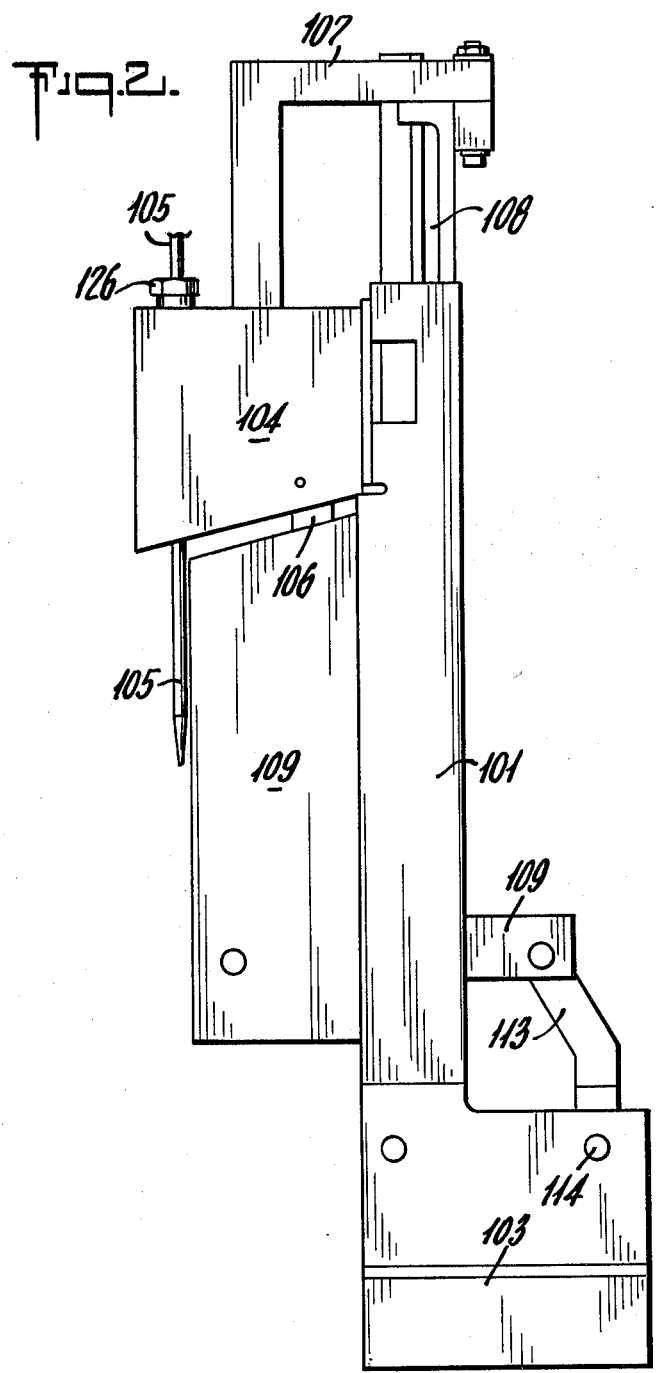

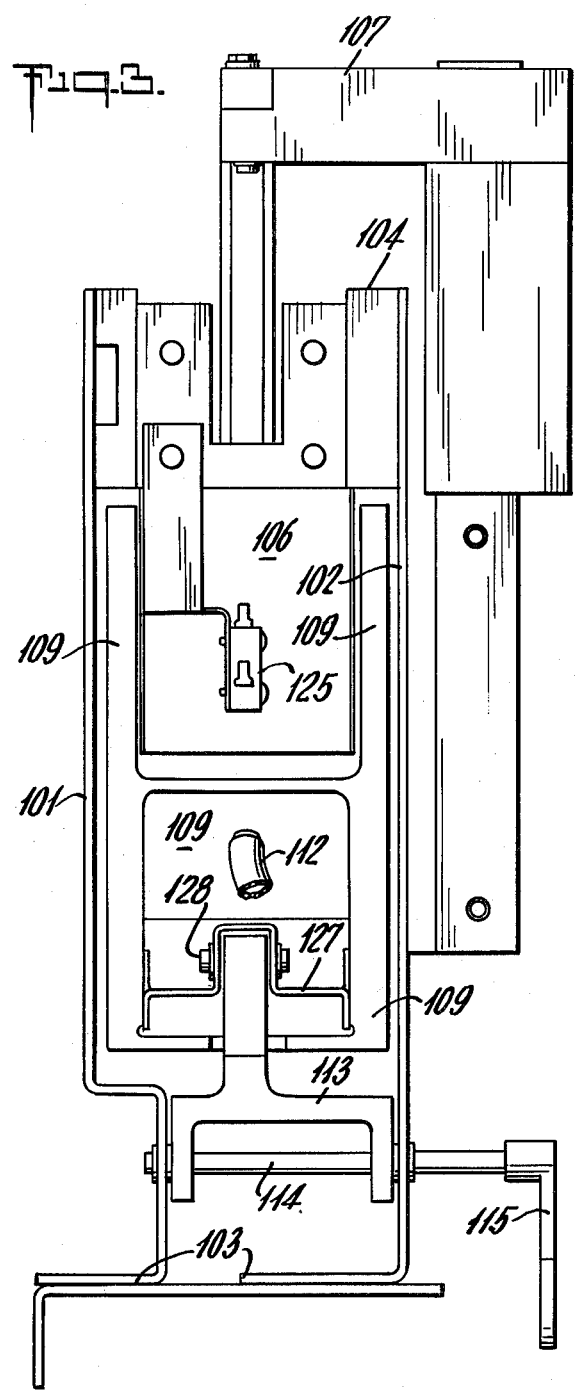

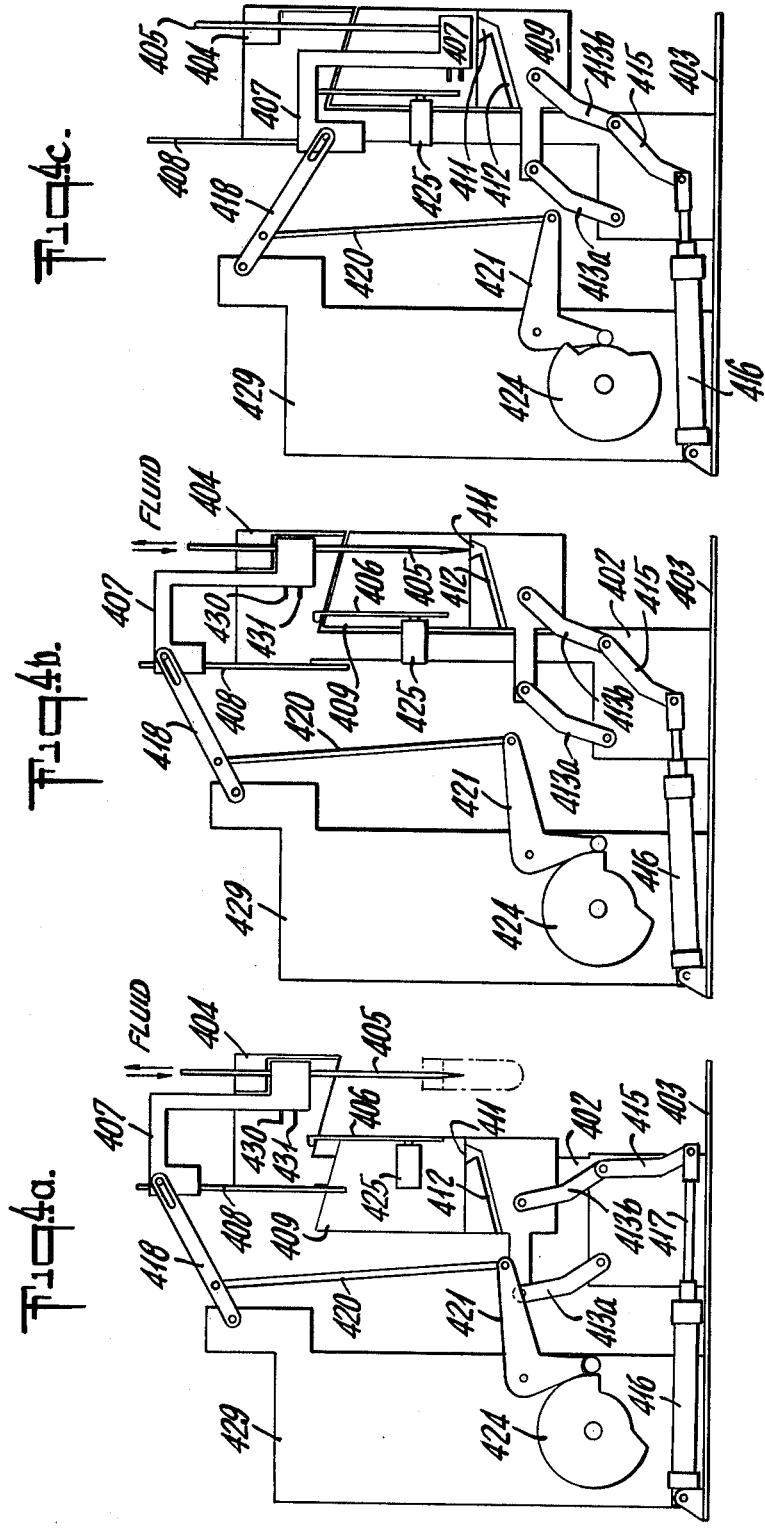

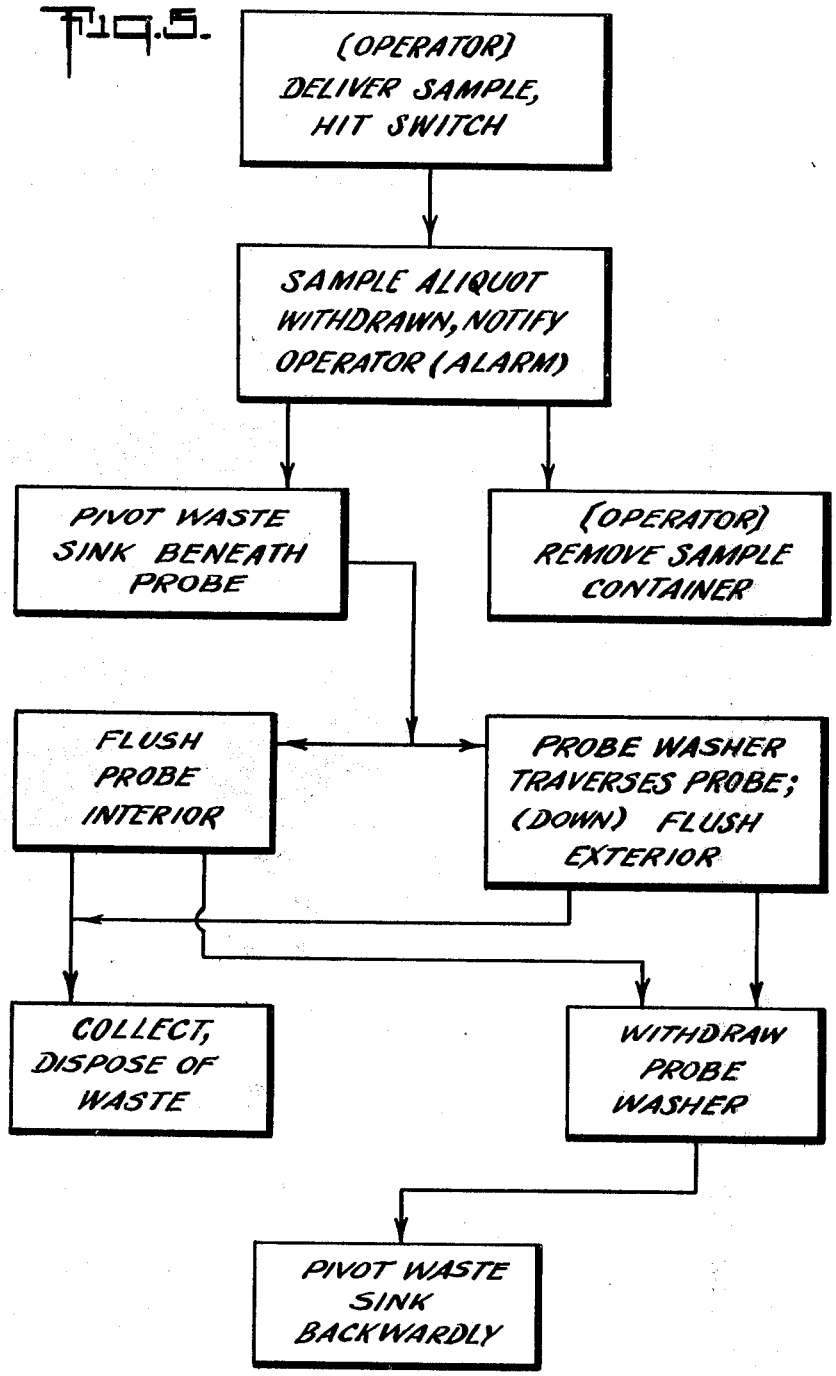

AUTOMATED, SELF-CLEANING FLUID SAMPLING APPARATUS

FIELD OF THE INVENTION

This invention relates to fluid sampling mechanisms, and more particularly to automated, self-cleaning mechanisms useful for the likes of clinical hematology instruments.

BACKGROUND OF THE INVENTION

In many field, there exists a need for efficient, reliable mechanisms for rapidly and repetitively sampling aliquots of fluid while avoiding contamination or intermixing between successive samples. One such field in which the need is particularly acutely felt is that of clinical hematology instrumentation. In this field, dictates of economics and cost effectiveness encourage nearly continuous machine operation, with blood samples from different patients being analyzed in rapid succession. Preferably this operation is conducted by a relatively unskilled operator who needs only to deliver the sample to an entry point, actuate a starting switch, and thereafter remove first the sample, and subsequently, a data card carrying the results of the tests performed by the instrument. Clearly, the very nature and criticality of hematology require extreme isolation between successive tests, for any intermixing of successive samples would surely result in improper data and incorrect diagnoses. On the other hand, manpower, practicality and economics dictate that the intersample cleanup be as simple, automatic, and rapid as possible.

It is an object of the present invention to provide automated, self-cleaning sampling apparatus which will permit the use of a large variety of sample containers and sample container configurations.

It is a further object that all portions of the sampling mechanism which make contact with the sample be thoroughly and automatically washed between samples, with minimal risk of intersample contamination.

It is a still further object that the automatic cleaning sequence be performed substantially independently of the control of the operator, yet be clearly visible and understandable to even the most unskilled of operators, whereby a subsequent cycle is not initiated until the previous, sample, clean, and dry cycles are completed.

It is yet another object of the present invention to provide a sampling system wherein the sample delivery process and actuation of the sampling and cleaning operations might be accomplished by one and the same hand of the operator.

These and other objects are substantially accomplished in accordance with the principles of the present invention.

DISCLOSURE OF THE PRESENT INVENTION

In accordance with the principles of the present invention, a downwardly suspended sampling probe is fixedly mounted on a first stationary member, control and actuation apparatus and linkages are maintained on a commonly based but rearwardly disposed second stationary member, and probe washing and waste removal assemblies are respectively slidably and pivotably carried on the first member. Accordingly, as the hand held sample is coupled to the probe, a substantially adjacent switch plate may be pressure actuated, thereby energizing the sample cleaning drying process. Upon such actuation, a sample aliquot is taken, and by suitable visual or audible warning, the operator is informed to remove the sample carrier. Thereupon, a waste-funnel-sink assembly is pivoted to a point beneath the probe, cleaning fluid is pumped through the inside of the probe, and a probe-washer assembly which envelops the probe slides downwardly along the probe while delivering cleaning fluids to the outside surfaces thereof. Once the cleansing fluids are carried away by the waste funnel-sink, and the washer assembly and waste removal assembly are returned to their respective original positions, indicating to the operator that the system is in condition for delivery of the next sample.

DESCRIPTION OF THE DRAWINGS

FIG. 2 shows a side view of the embodiment of FIG. 1;

FIG. 3 shows a rear view of the apparatus of FIG. 1;

FIGS. 4A through 4C show an alternative embodiment of the principles of the present invention, wherein an illustrative sequential operation is illustrated, with FIG. 4A depicting the system in condition for operation, FIG. 4B depicting the system after sample withdrawal, with a waste removal assembly moved into position for initiation of the cleaning cycle, and FIG. 4C depicting the system during the process of probe cleansing;

FIG. 5 shows an illustrative procedural sequence for the operation of the embodiments previously referenced;

BEST MODE FOR PRACTICING THE INVENTION

Figure 1:
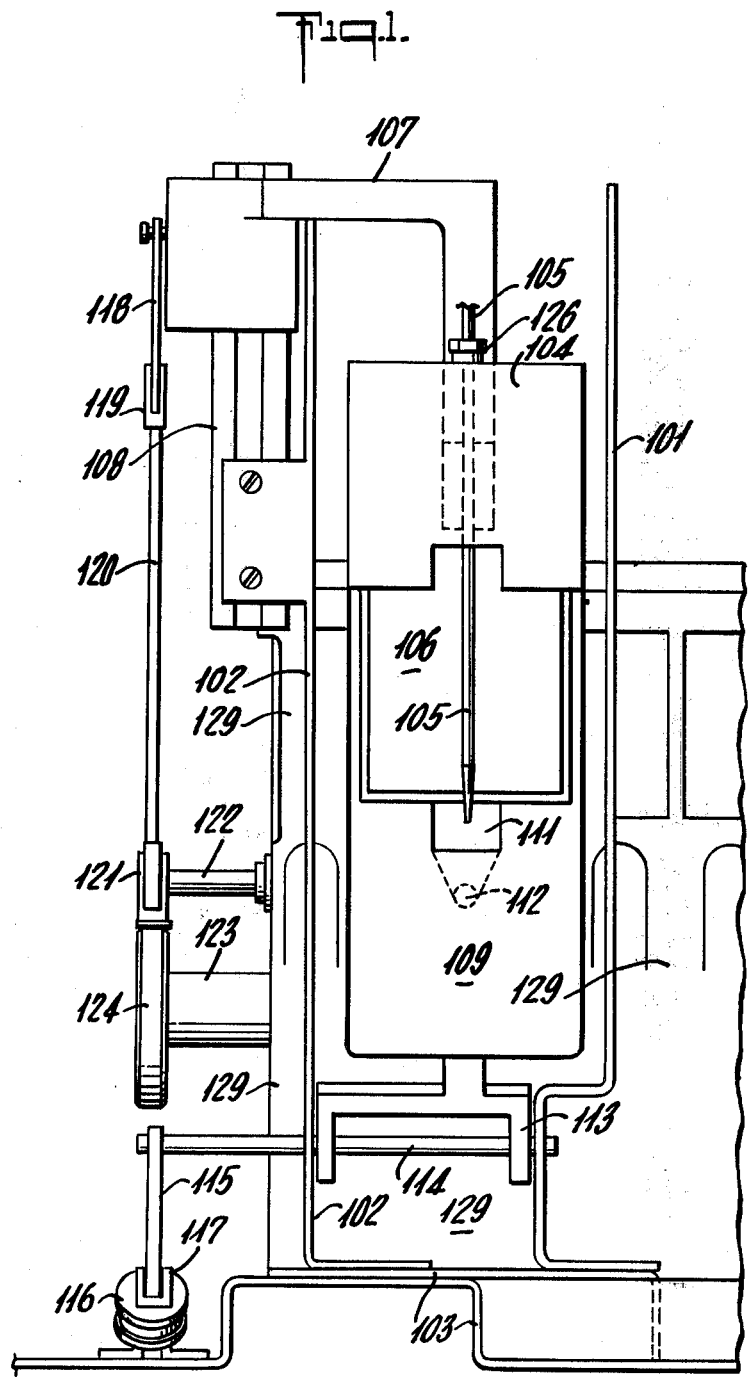
FIG. 1 shows a front view of a preferred embodiment of the principles of the present invention.

Referring generally to the drawings, there is shown in various isometric, cutaway, and symbolic views, apparatus which illustrates the structure and preferred mode of operation in accordance with the principles of the present invention. It will be noted that FIGS. 1-3 show respective front, side, and rear isometric views (the latter two views omitting for clarity the rear stationary member 129 of FIG. 1). FIGS. 4A-4C show cutaway views of an alternative embodiment, which in salient respects is substantially identical to the embodiment of FIGS. 1-3, but which is structurally simplified somewhat for purposes of clarity in explaining sequential operation, and which includes somewhat differently structured, but functionally identical linkage mechanisms. In the embodiment of FIGS.4A-4C, parts whiich are the functional or structural analogs of respective parts in the FIG. 1-3 embodiment are similarly numbered, except utilizing the "400" series of prefixes, rather than the "100" series of prefixes utilized in accordance with the embodiment of FIGS. 1-3.

In the embodiment of FIGS. 1-3, a front stationary member or tower is defined by fixed vertical portions 101 and 102, and is secured to a suitable base 103. This front tower 101 and 102 carries the sampling probe 105 on a forwardly extending cantilever portion 104. Rearwardly of the probe 105, the cantilever portion 104 also carries a pivoting actuation plate 106 and immediately therebehind, an actuation switch 125 which is operated by the pivoting plate 106. A waste disposable sink 109, defining a waste receptacle funnel 111 and conduit 112, is pivotably carried by a waste lever 113, which in turn is pivotably mounted to vertical support members 101 and 102 at transverse shaft 114. Vertical support member 102 has attached thereto a sliding track 108, onto which is mounted, in slidable fashion, an exterior probe washer assembly 107. It will be appreciated that the assembly 107 includes respective integral sections which ride on the slide track 108, which extend between the track 108 and the area of the probe 105, and which envelope the exterior of the probe itself. Not shown in FIGS. 1-3, but evident from the embodiment of FIGS. 4A-4C, the exterior probe washer assembly 107 is provided with respective cleansing fluid and drying gas feeds, which are coupled to the segment of assembly 107 which envelops the exterior of the probe 105.

Figure 6B:
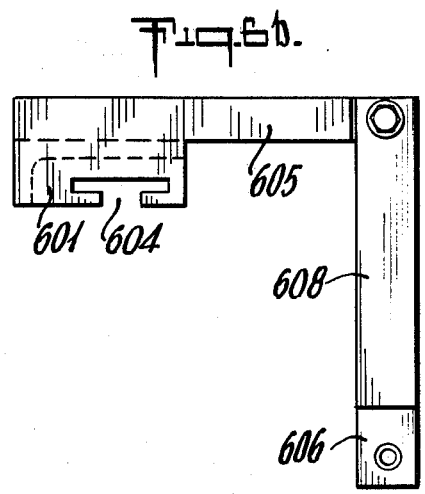
FIG. 6A through 6C show three views of a preferred probe exterior washer component.
Figure 6A:
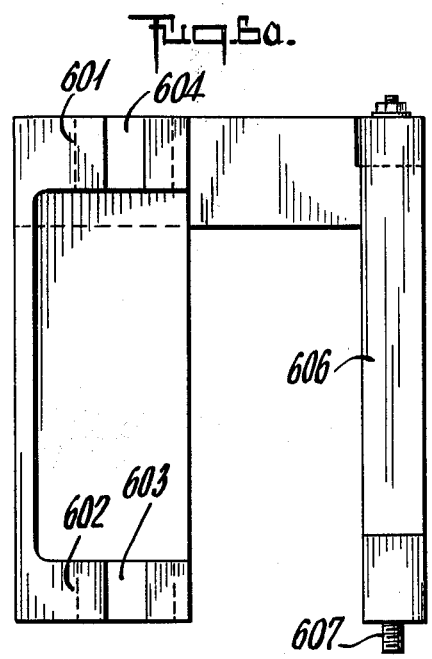
Figure 6C:
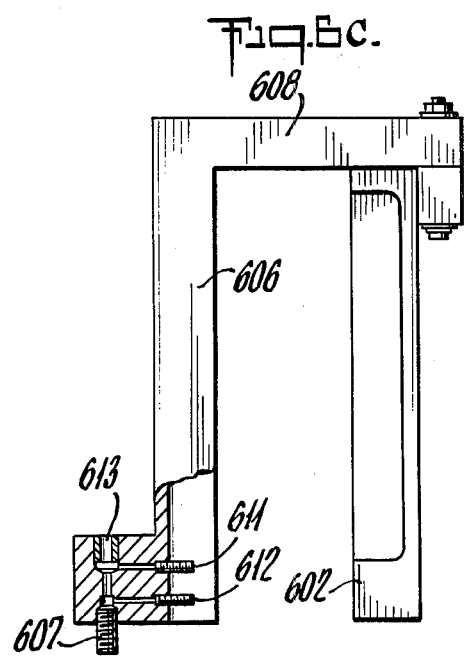

FIGS. 6A-6C show respective front, side, and top views of a preferred configuration for the probe exterior washer assembly 107. From those figures, the relative configuration of a slot 604 and 603 and clevises 601 and 602 are provided to mate with the track 108, and arms 605, 608, and 606 carry the segment 613 and 607 wherein passes the probe 105, with air being delivered at port 611 and fluid at port 612.

Figure 7:
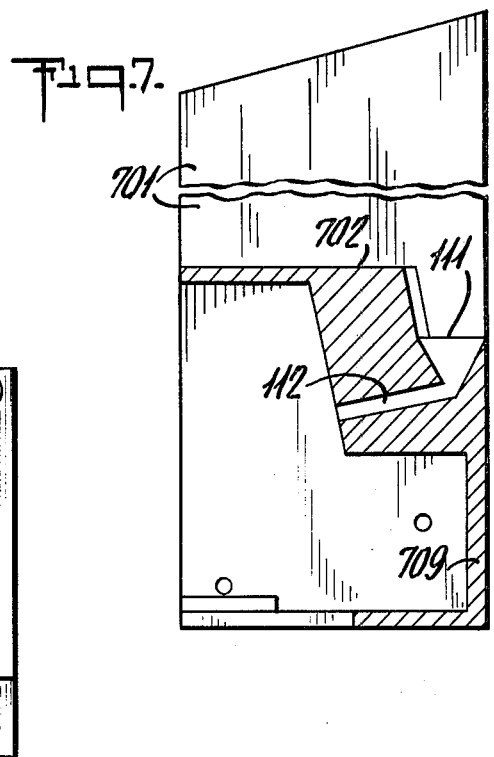
FIG. 7 shows, in cross section, a preferred waste removal component.

FIG. 7 shows a preferred construction, in cross-section, of the waste assembly 109, including funnel 111 and conduit 112, and exterior walls 701, 702, and 709.

As may be most clearly seen from FIGS. 2 and 3, the waste funnel-sink assembly 109 is pivotable, by virtue of lever 113 and its pivot shafts 114 and 128, between a rearward most position as shown in FIG. 2, and a more forward position wherein the funnel 111 is disposed substantially directly under the probe 105. This operation is more clearly evident from the embodiment of FIGS. 4A-4C, discussed hereinafter. Likewise, the up and down sliding motion of exterior probe washer assembly 107, both along track 108 and along the probe 105, is clearly evident upon consideration of the embodiment of FIGS. 4A-4C.

The embodiment of FIG. 1 also shows a second or rear stationary member or tower 129, which is disposed behind the first stationary member 101 and 102, and which also is suitably secured to the base member 103. The second or rear stationary tower 129 is adapted to carry the mechanical and/or electrical control mechanisms whereby the exterior probe washer assembly 107, and the waste funnel-sink assembly 109 are operated, and also in accordance therewith, whereby conventional pumps are actuated for the fluid sampling operation, the provision of cleaning fluids within and without the probe 105, and (optionally) the provision for forced drying gases (i.e. air) within and without the probe.

In a preferred embodiment, the rear stationary tower 129 includes a principal control cam shaft 123, which includes, among others, a cam 124 which via a cam follower 121 and linkage rods 120 and 118, provides motivation and control of the positioning of the exterior probe washer assembly 107. Not shown in the embodiment of FIGS. 1-3, but well within the capability of those of ordinary skill in the art, are a sequence of cams, suitably configured and mounted on shaft 123, whereby the various sampling, cleansing, and pumping operations are actuated in coordinated sequence with the operation of the exterior probe washing assembly 107. Likewise, the pivotable operation of lever 113, and hence of the waste funnel-sink assembly 109 may be so controlled preferably by means of a compressed air cylinder 116 and piston 117, through linkage 115 and shaft 114. In a preferred embodiment, the cylinder 116 is actuated by appropriate movement of a cam (not shown) on shaft 123. Hence, in a preferred mode of operation, operator exerted pressure against plate 106 operates switch 125, in turn energizing a motor (not shown) within member 129, and turning cam shaft 123 for one or more full revolutions. In accordance with the ability of one of ordinary skill in the art, the various sequences of operations set forth herein are thereby initiated and respectively accomplished. It will also be evident that it is well within the ability of those of ordinary skill in the art, as an alternative to the cam shaft actuated control, to provide suitable relay, electronic, or programmed sequencing control for accomplishment of the various operations specified herein, especially the various sampling, cleaning, and drying pumping operations. In the event that such electrical control is to be utilized, it will be appreciated that provision would also be made for electrical or optical sensors at various positions throughout the apparatus, thereby to detect and responsively to control the location, movement, and operation of the various portions of the apparatus, especially the exterior probe washer assembly 107 and the waste funnel-sink assembly 109.

Referring next to FIGS. 4A-4C, operation in accordance with the principles of the present invention may be better appreciated. FIGS. 4A-4C represent partially cutaway side views, whereby for convenience the cam, cylinder, and various linkage mechanisms are shown, in conjunction with cutaway views of the various support, cleaning, waste disposal and probe/actuation aspects. Also, for convenience of explanation, the structural detail of the apparatus of FIGS. 4A-4C has been somewhat simplified.

The principal difference between the embodiment of FIGS. 1-3 and that of FIGS. 4A-4C resides in the linkage mechanism between the air cylinder which actuates the waste funnel-sink assembly, and that assembly itself. Whereas in FIGS. 1-3, a single lever 113 was employed, in the embodiment of FIGS. 4A-4C, a "four bar" linkage 413A and 413B is employed. It will be appreciated by those of ordinary skill in the art that either such linkage assembly, or many of their various structural and functional equivalents, may be utilized.

FIG. 4A shows the apparatus at a "ready" position, with the exterior probe washer 407 disposed at its upward most position along track 408 and correspondingly along probe 405. Similarly, the waste funnel-sink assembly 409 is in its rearward most position, out of the way and allowing the operator free access to the probe 405. For commencement of operation, the operator grasps a vial of blood or the like fluid to be analyzed, placing it generally in the position shown in phantom in FIG. 4A. It will be apparent that when the vial is being held in such position, the index finger or the like can be conveniently extended to make contact with the switchplate 406, the depression of which in turn actuates switch 425. Thereupon, an automatic sequence of events commences, the first event of which is actuation of a pump (not shown) which withdraws a predetermined aliquot of fluid (e.g. blood) from the vial via the probe 405. When the aliquot has been withdrawn, a suitable alarm is actuated, warning the operator to remove the vial so that the cleaning operation may commence.

Referring next to FIG. 4B, there is shown the result of the next set of operations, wherein air cylinder 416 is actuated to withdraw piston 417, thereby to pivot waste funnel-sink assembly 409 forwardly, into position whereby the waste disposal funnel 411 and disposal conduit 412 are located generally beneath the probe 405. Either at this time or during the next subsequent steps, cleansing fluid (e.g. water) is backflushed through the probe 405, thereby to cleanse the interior of the probe, with the waste being collected in funnel 411 and suitably disposed of via conduit 412. Preferably, this backflushing of fluid occurs simultaneously with the cleansing of the exterior of probe 405.

Referring next to FIG. 4C, there is shown the positioning of the probe exterior washer 407 at the termination of the exterior wash cycle. That is, as cam follower 421 indexes to the inner surface of cam 424, and passes therealong, connecting rod 420 is pulled downwardly, linkage bar 418 is correspondingly pivoted, and the probe washer 407 is maneuvered downwardly on track 408, and simultaneously along the probe 405. During the time of this traversal, pressurized air is supplied at port 430, and pressurized water at port 431, thereby to cleanse and dry the exterior of probe 405. Again, waste is collected at funnel 411 and disposed of via conduit 412.

It will be appreciated that in accordance with the abilities and knowledge of those of ordinary skill in the art, the cam 424 may be configured in a variety of ways, whereby the rate of traversal of assembly 407 along probe 405 may be controlled, and furthermore, by coordinating such traversal with the delivery of air and fluid to ports 430 and 431 (e.g. by other cams located on the same cam shaft), the rate, extent, and duration of the cleansing operation may be regulated.

Upon completion of the cleansing cycle, assemblies 407 and 409 are returned to the position shown in FIG. 4A, either simultaneously or in sequence, as desired, and the mechanism is once more in condition for receipt of a new sample. It will be appreciated that provision of pressurized air at port 430 may be utilized, if desired, as an additional drying step. Likewise, it may be desirable to backflush air through the probe 405 to eliminate residual fluids therein.

A preferred mode of sequential operation for the embodiments of FIGS. 1-3 and 4A-4C is set forth in FIG. 5. As shown in that figure, the operator first delivers the sample, hits the start switch, and the machine commences sampling of an aliquot of fluid. When the sample has been withdrawn, an alarm notification is given, and the operator removes the sample vial or container. The waste sink is then pivoted beneath the probe, and either simultaneously or in desired sequence, the probe interior is flushed, and the probe washer traverses the probe downwardly, flushing and cleaning the exterior of the probe. During such time, waste is collected and disposed of, whereupon the probe washer is withdrawn upwardly and the waste sink is pivoted backwardly.

The foregoing has set forth illustrative and preferred embodiments of the present invention, but it will be understood that numerous alternative embodiments will occur to those of ordinary skill in the art without departure from the spirit or scope of the principles of the present invention.

What is claimed is:

1. Automatic self-cleaning liquid sampling apparatus comprising:
    (a) a first stationary member including a fixed downwardly suspended sampling probe, energizing switch means proximate said probe, and a slide track generally parallel said probe;
    (b) a second stationary member generally posterior said first stationary member, including a motor, cam means operated by said motor, and a piston-cylinder drive means;
    (c) probe washer means, movable along said slide track, including a portion which envelops said probe and which slides along said probe as said probe washer means moves on said slide track;
    (d) linkage means for moving said washer means along said slide track under motivation of said cam means;
    (e) waste collection means, pivotable under motivation of said piston-cylinder drive means, to a position beneath said probe;
    (f) means for supplying cleansing fluids to said probe and to said washer means for application to said probe; and
    (g) control means, energized by said switch means, for selectively enabling said motor, said drive means, and said means for supplying in predetermined time sequences with respect to one another.

2. Apparatus as described in claim 1 wherein said means for supplying comprises means for supplying cleaning solution and drying gas to the interior of said probe means, and to said washer means for application to the exterior of said probe means.

3. Apparatus as described in claim 1 wherein said probe comprises an elongated, substantially vertical tube opening at a lowermost extremity for drawing samples, wherein said slide track comprises a substantially vertical track generally posterior said probe and parallel to but at least partially above said probe, and wherein said washer means is arranged to have said portion fully traverse said probe as said washer means fully traverses said track for each motivation cycle of said cam means.

4. Apparatus as described in claim 3 wherein said collection means includes a plural arm pivot assembly interconnecting said collection means with said first stationary member, at a location generally posterior and beneath said opening of said probe, and wherein said collection means is pivotable upwardly and forwardly to a location beneath said probe opening.

5. Apparatus as described in claims 1 or 4 wherein said first stationary member defines a void to provide an area for collection of samples, said probe penetrating said void from above, said switch means being located in the posterior region of said void adjacent said probe, said collection means being pivotable between a position below said switch means behind said void, and a position in said void beneath said probe, said collection means including side and bottom portions for collection and disposition of fluids from said probe.

* * * * *